United States Patent [19]
Gorman et al.

[11] Patent Number: 5,952,217
[45] Date of Patent: Sep. 14, 1999

[54] RECOMBINANT YEAST CELL AND ASSAY USING SAME

[75] Inventors: Jessica A. Gorman, Yardley, Pa.; Susan Manly, Wallingford, Conn.

[73] Assignee: Bristol-Myers Squibb Company, Princeton, N.J.

[21] Appl. No.: 08/935,760

[22] Filed: Sep. 23, 1997

[51] Int. Cl.⁶ .............................. C12N 1/14; C12N 15/00; C12Q 1/48; C12P 21/06
[52] U.S. Cl. ..................... 435/254.2; 435/15; 435/69.1; 435/252.3; 435/320.1; 435/194; 536/23.2
[58] Field of Search .............................. 435/254.2, 252.3, 435/320.1, 194, 15, 69.1; 536/23.2

[56] References Cited

FOREIGN PATENT DOCUMENTS

WO94/05811  3/1994  WIPO.

OTHER PUBLICATIONS

Bagrodia et al. (1995) J. Biol. Chem. 270;22731–22737.
Murayama et al. (1996) Gerontology 42:2–11.
Bagrodia et al. (1995) J. Biol. Chem. 270:27995–27998.
Brown et al. (1996) Current Biol. 6:598–605.
Cvrckova et al. (1995) Genes & Development 9:1817–1830.
Harden et al. (1996) Mole. and Cell. Biol. pp. 1896–1908.
Knaus et al. (1995) Science 269:221–223.
Kohler et al. (1996) Proc. Natl. Acad. Sci. USA 93:13223–13228.
Leberer et al. (1992) The EMBO Journal 11:4815–4824.
Leberer et al. (1996) Proc. Natl. Acad. Sci. USA 93:13217–13222.
Manser et al. (1994) Nature 367:40–46.
Manser et al. (1995) J. Biol. Chem. 270:25070–25078.
Marcus et al. (1995) Proc. Natl. Acad. Sci. USA 92:6180–6184.
Martin et al. (1995) The EMBO Journal 14:1970–1978.
Mosch et al. (1996) Proc. Natl. Acad. Sci. USA 93:53522–5356.
Ottile et al. (1995) The EMBO Journal 14:5908–5919.
Ramer et al. (1993) Proc. Natl. Acad. Sci. USA 90:452–456.
Teo et al. (1995) J. Biol. Chem. 270:26690–26697.
Wu et al. (1995) J. Biol. Chem. 270:15984–15992.
Zhang et al. (1995) J. Biol. Chem. 270:23934–23936.
Zhao et al. (1995) Mole. and Cell. Biol. 15:5246–5257.

*Primary Examiner*—Ponnathapura Achutamurthy
*Assistant Examiner*—Tekchand Saidha
*Attorney, Agent, or Firm*—Thomas R. Savitsky; Christopher A. Klein; Joseph M. Sorrentino

[57] ABSTRACT

Yeast cell having the ability to express the kinase domain of N-Pak. The expressed kinase domain restores the mating function of a ste20 mutant and such cells are therefore useful in an assay to screen for inhibitors of N-Pak. Such inhibitors may be useful in treatment and/or prevention of Alzheimer's Disease.

24 Claims, 1 Drawing Sheet

RECOMBINANT YEAST CELL AND ASSAY USING SAME

FIELD OF THE INVENTION

The present invention concerns expression vectors containing a yeast promoter and nucleic acid encoding the kinase domain of mammalian N-Pak, recombinant yeast host cells expressing the N-Pak kinase domain, and assays to detect inhibitors of N-Pak activity.

BACKGROUND OF THE INVENTION

Rac and Cdc42 are members of the Rho family of small GTP binding proteins. These GTPases are involved signal transduction processes affecting morphogenesis and assembly of cytoskeletal structures involved in cell motility and metastasis. Recently, a family of serine/threonine protein kinases characterized by their binding to Cdc42 and Rac have been described. Based upon this characteristic, they have been named p21-activated kinases (PAK). These constitute a new subfamily of kinases, characterized by high homology to the *Saccharomyces cerevisiae* Ste20 kinase.

A mammalian PAK ($p65^{PAK}$) was identified by its specific binding to GTP-bound forms of Cdc42 and Rac1 (Manser et al, 1994). Previously, a gene for a second member of this family was isolated from a rat brain cDNA library based on its ability to interact specifically with the C-terminal portion of the Alzheimer β amyloid precursor protein (a fragment comprising the C-terminal 100 amino acids of β-APP). The gene encoding this protein appears to be specifically expressed in neuronal tissue. The sequence which was found to be closely related to that of $p65^{PAK}$ and to the yeast STE20 gene product (Ramer and Davis, 1993), was designated N-Pak (nervous system specific $p^{21}$ activated kinase). The sequence of this N-Pak cDNA clone and corresponding amino acid sequence are disclosed in WO 94/05811, U.S. patent application Ser. Nos. 08/559,397, 08/144,555, and 07/938,184, the disclosures of which are incorporated herein by reference in their entirety.

In the last few years, numerous additional PAKs, characterized by the presence of a sequence conserved C-terminal kinase domain and upstream p21-binding and activation domains, have been reported. Thus, these kinases comprise a ubiquitous new family of serine/threonine kinases, referred to as the PAK/Ste20 family. Three mammalian isoforms have been described to date. In rodents, the 68-kDa α-PAK (Manser et al, 1994) and the 65 kDa β-PAK (Manser et al, 1995; Bagrodia et al, 1995a) appear to be enriched in brain, while the 62 kDa γ-isoform (Teo et al, 1995) is widely expressed in all tissues. Human homologues of the rat α-isoform, hPAK1 (Brown et al, 1996) and the γ-isoforms hPAK2 (Knaus et al, 1995) and hPAK65 (Martin et al, 1995) have been described.

In addition to the numerous vertebrate species now shown to have PAK kinases, homologues have been described in insects such as Drosophila (Harden, et al. 1996) and several fungal species. Genes encoding Ste20 homologues have been isolated from the budding yeast *S. cerevisiae* (Ramer and Davis 1993; Cvrckova, et al, 1995), the fission yeast *Schizosaccharomyces pombe* (Ottilie et al, 1995; Marcus et al 1995) and the dimorphic human opportunistic pathogenic yeast *Candida albicans* (Leberer et al, 1996; Kohler and Fink, 1996)

In budding yeast, the Ste20 protein is a component of a MAPK signal transduction pathway leading to mating (Ramer and Davis, 1993). This pathway is activated by hormone stimulation of a trimeric G protein coupled mating receptor. Ste20 serves as a link between Gβγ and downstream mitogen-activated protein kinases of this well-studied signalling cascade and is therefore essential for activation of mating specific genes (Leberer et al, 1992; Wu et al, 1995). Recent evidence suggests an additional role for Cdc42 and Ste20 or Ste20 homologues in yeast morphogenesis (Cvrckova et al, 1995; Mosch, H-Uet al, 1996). Likewise, in fission yeast, disruption of the pak1 gene causes aberrant actin localization and reduces mating (Marcus et al, 1995; Ottilie et al, 1995).

Recent evidence suggests a role for mammalian Paks in signalling to p38 and JNK MAP kinases (Zhang et al, 1995; Bagrodia et al, 1995b; Brown et al, 1996). In addition, human PAK1 and PAK2 have been shown to be regulated by G-protein coupled receptors (Knaus et al, 1995). Therefore, there appears to be a common role for the PAK family members in signalling pathways which utilize Cdc42 and Rac1.

Given the homology of mammalian PAK family proteins to the yeast Ste20 protein, the ability of the mammalian protein to substitute for the yeast protein has been examined. Zhao et al, (1995) found that the rat p65PAK was unable to complement a *S. cerevisiae* ste20 mutant. They postulated that the mammalian enzyme was unable to phosphorylate the appropriate downstream target. Subsequently, the mouse gene m-PAK-3 was tested in a similar manner and found to give extremely weak suppression of the mating defect; mating occurred at a level that was 3–4% of a wild type strain (Bagrodia et al, 1995a). Brown et al (1996) reported that full length hPAK can restore mating of a ste20-null mutant to nearly normal wild type levels. This led these authors to suggest that the differences in amino acids (8 out of 545) between rat and human might be sufficient to account for this difference, and that one or more of these differences might define residues important for protein-protein interaction.

The establishment of this class of serine/threonine kinases as important intermediates in cell signal transduction has generated much interest in their activity and role in a variety of cellular processes such as differentiation, cytoskeletal assembly, motility and growth, particularly in light of the finding that the brain specific N-Pak protein binds specifically to the cytoplasmic domain of β-APP. Heretofore, the expression of rat N-PAK in yeast has been unknown. We have discovered that N-PAK truncated to exclude the N-terminal region containing the Cdc42 binding domain can functionally substitute for the yeast Ste20 protein.

REFERENCES

Bagrodia, S., S. J. Taylor, C. L. Creasy, J. Chernoff and R. A. Cerione (1995a) Identification of a mouse p21 Cdc42/Rac activated kinase. J. Biol. Chem 270:22731–22737.

Bagrodia, S., B. Derijard, R. J. Davis and R. J. Cerione (1995b) Cdc42 and PAK-mediated signalling leads to JNK and p38 mitogen-activated protein kinase activation. J. Biol. Chem 270:27995–27998.

Brown, J. L., L. Stowers, M. Baer, J. Trejo, S. Coughlinand and J. Chant. (1996) Human Ste20 homologue hPAK1 links GTPases to the JNK MAP kinase pathway. Current Biology 6:598–605.

Cvrckova, F., CIDe Virgilio, E. Manser, J. R. Pringle and K. Nasmyth (1995) Ste20-like protein kinases are required for normal localization of cell growth and for cytokinese in budding yeast. Genes and Devel. 9:1817–1830.

Harden, N., J. Lee, H. Y. Loh, Y-M.Ong, I. Tan, T. Leung, E. Manser and L. Lim. (1996) A Drosophila homologue of the Rac- and Cdc42-activated serine/threonine kinase PAK is a potential focal adhesion and focal complex protein that colocalizes with dynamic actin structures. Molec. Cell. Biol. 16:1896–1908.

Knaus, U. G., S. Morris, H-J Dong, J. Chernoff and G. M. Bokoch (1995) Regulation of human leukocyte p21-activated kinases through G protein-coupled receptors. Science 269:221–223.

Kohler, J. R. and G. R. Fink (1996) *Candida albicans* strains heterozygous and homozygous for mutations in mitogen-activated protein kinase signalling components have defects in hyphal development. Proc. Natl. Acad. Sci. USA 93:13223–13228.

Leberer, E., D. Dignard, D. Harcus, D. Y. Thomas and M. Whiteway. (1992) The protein kinase homologue Ste20 p is required to link the yeast pheromone response G-protein βγ subunits to downstream signalling components. EMBO. J. 11:4815–4824.

Leberer, E, D. Harcus, I. D. Broadbent, K. L. Clark, D. Dignard, K. Ziegelbauer, A. Schmidt, N. P. Gow, A. P. Brown and D. Y. Thomas. (1996) Signal transduction through homologues of the Ste20 and Ste7 protein kinases can trigger hyphal formation in the pathogenic fungus *Candida albicans*. Proc. Natl. Acad. Sci. USA 93:13217–13222.

Manser, E., T. Leung, H. Salihuddin, Z-S. Zhao and L. Lim (1994) A brain serine/threonine protein kinase activated by Cdc42 and Rac1. Nature 367:40–46.

Manser, M., C. Chong, Z-S. Zhao, T. Leung, G. Michaels, C. Hall and L. Lim. (1995) Molecular cloning of a new member of the p21-Cdc42/Rac-activated kinase (PAK) family. J. Biol. Chem.:270:25070–25078.

Marcus, S., A. Polverino, E. Chang, D. Robbins, M. H. Cobb and M. Wigler. (1995) Shk1, a homologue of the *Saccharomyces cerevisiae* Ste20 and mammalian P65PAK protein kinases, is a component of a Ras/Cdc42 signalling molecule in the fission yeast *Schizosaccharomyces pombe*. Proc. Natl. Acad. Sci. USA 92:6180–6184.

Martin, G. A., G. Bollag, F. McCormick and A. Abo. (1995) A novel serine kinase activated by rac1/CDC42Hs-dependent autophosphorylation is related to PAK65 and STE20. EMBO J. 14:1970–1978.

Mosch, H-U., R. L. Roberts and G. R. Fink (1996) Ras2 signals via the Cdc42/Ste20/mitogen activated protein kinase module to induce filamentous growth in *Saccharomyces cerevisiae*. Proc Natl. Acad. Sci. USA 93:5352–5356.

Ottilie, S., P. J. Miller, D. O. Johnson, C. L. Creasy, M. A. Sells, S. Bagroda, S. Forsburg and J. Chernoff. (1995) Fission yeast pak1$^+$ encodes a protein kinase that interacts with Cdc42p and is involved in the control of cell polarity and mating. EMBO J. 14:5980–5919.

Ramer, S. W. and R. W. Davis (1993) A dominant truncation allele identifies a gene, STE20, that encodes a putative protein kinase necessary for mating in *Saccharomyces cerevisiae*. Proc. Natl. Acad. Sci, USA 90:425–456.

Teo, M., E. Manser and L. Lim (1995) Identification and molecular cloning of a p21cdc42/rac- activated serine threonine kinase that is rapidly activated by thrombin in platelets. J. Biol. Chem 270: 26690–26697.

Wu, C., M. Whiteway, D. Y. Thomas and E. Leberer (1995) Molecular characterization of Ste20p, a potential mitogen-activated protein or extracellular signal related kinase kinase (MEK)kinase kinase from *Saccharomyces cerevisiae*. J. Biol. Chem. 270:15984–15992.

Zhang, S., J. Han, M. A. Sells, J. Chernoff, U. G. Knaus, R. J. Ulevitch and G. M. Bokoch. (1995) Rho family GTPases regulate p38 mitogen-activated protein kinase through the downstream mediator Pak1. J. Biol. Chem 270:23934–23926.

Zhao, Z-S., T. Leung, E. Manser and L. Lim (1995) Pheromone signalling in *Saccharomyces cerevisiae* requires the small GTP-binding protein Cdc42p and its activator CDC24 Molec. Cell. Biol. 15:5246–5257.

SUMMARY OF THE INVENTION

The mammalian neuronal specific serine/threonine kinase N-Pak has high homology to the yeast *Saccharomyces cerevisiae* STE20 gene product. Ste20 acts as a signalling molecule in the yeast mating signal transduction pathway, where it comprises the first kinase (MAPKKKK) in a phosphorylation cascade. We have discovered that the kinase domain of the mammalian N-Pak protein can suppress the mating defect of a yeast mutant functionally deficient for the STE20gene. Restoration of signal transduction was demonstrated by the ability to mate at high frequency as well as by activation of a reporter gene (e.g., lacZ) regulated by a yeast promoter (e.g., the promoter region of a phermone inducible yeast gene).

Thus, the present invention is directed to a recombinant yeast host cell comprising recombinant nucleic acid encoding the kinase domain of mammalian N-Pak or homolog thereof, wherein, when expressed said kinase domain or homolog thereof has serine/threonine kinase activity but no Cdc42 binding activity.

The present invention is also directed to an expression vector comprising a yeast promoter and nucleic acid encoding the kinase domain of mammalian N-Pak or homolog thereof, wherein, when expressed said kinase domain or homolog thereof has serine/threonine kinase activity but no Cdc42 binding activity.

Further, the present invention is directed to a method for identifying a compound that interferes with the activity of mammalian N-Pak comprising:

(a) incubating a recombinant yeast cell that expresses the binding domain of mammalian N-Pak or functional homolog thereof with a test compound;

(b) determining whether the mating signal transduction pathway is inhibited relative to a control without the test compound.

BRIEF DESCRIPTION OF THE DRAWING

FIG. 1:

Schematic representation of plasmid pJG215

DETAILED DESCRIPTION OF THE INVENTION

Figure 1:
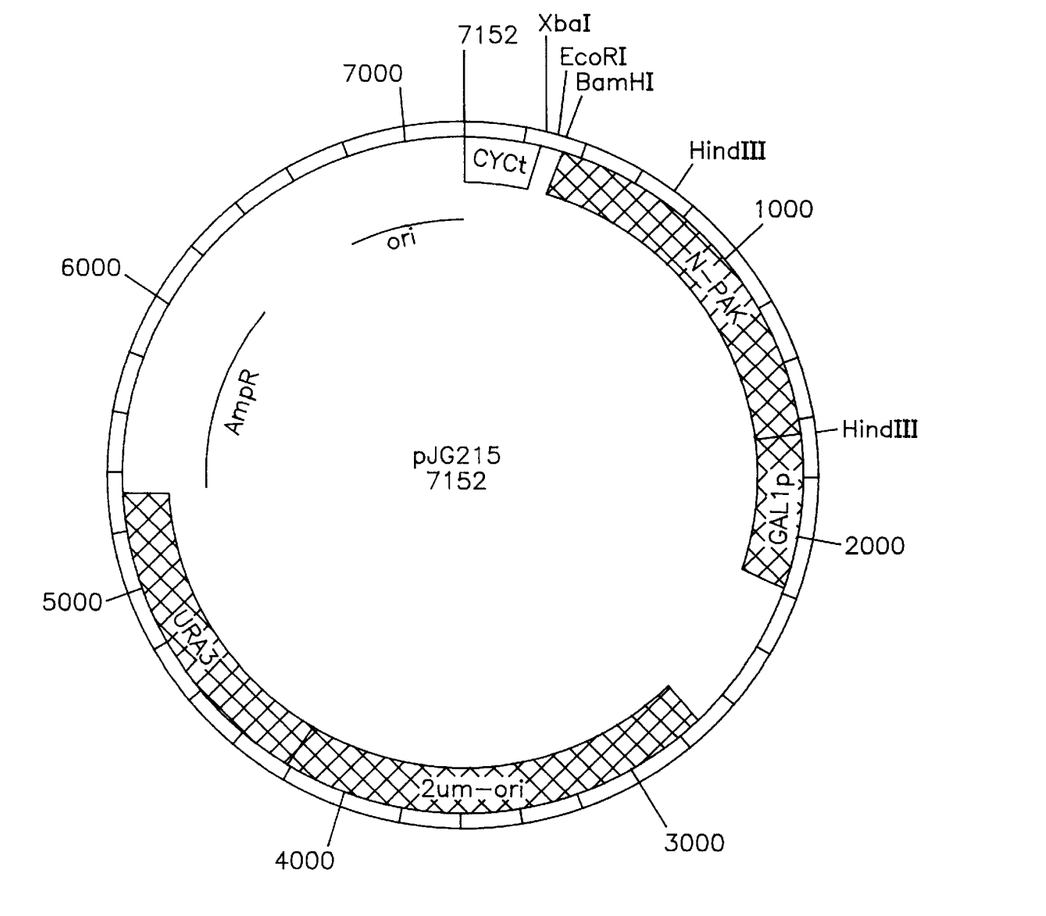

All DNA sequences are represented herein by formulas whose left to right orientation is in the conventional direction of 5' to 3'. Nucleotide base abbreviations used herein are conventional in the art, i.e., T is thymine, A is adenine, C is cytosine, and G is guanine.

It is also contemplated that the present invention encompasses modified sequences. As used in the present application, the term "modified", when referring to a nucleotide sequence, means a nucleotide sequence which differs from the wild-type sequence found in nature. The DNA sequences of the present invention can be obtained using various methods well-known to those of ordinary skill in the art. The expression vectors can be partly or wholly synthesized chemically and/or partly or wholly prepared through genetic engineering techniques. Fragments can be sequentially ligated (via appropriate terminal restriction sites or complementary terminal sequences) so as to form the correct linear sequence of nucleotides.

The sequences of the present invention can also be modified (i.e., mutated) to prepare various mutations. These mutations may permit higher levels of production of the expressed peptide, easier purification of the peptide, or provide additional restriction endonuclease recognition sites. All such modified DNA and polypeptide molecules are included within the scope of the present invention.

Expression vectors

Expression vehicles of the invention for production of the kinase domain of mammalian N-Pak include plasmids or other vectors. In general, such vectors contain control sequences that allow expression in various types of hosts. Suitable expression vectors containing the desired coding and control sequences may be constructed using standard recombinant DNA techniques known in the art, many of which are described in Sambrook et al. (1989), *Molecular Cloning: A Laboratory Manual,* 2nd edition, Cold Spring Harbor Laboratory, Cold Spring Harbor, N.Y.

An expression vector as contemplated by the present invention is at least capable of directing the replication of the vector in both bacteria and yeast and expression of the DNA sequence of interest in yeast. One class of vectors utilizes yeast DNA elements that provide autonomously replicating origins such as the yeast $2\mu$ element or ARS1 sequence which yield extrachromosomal plasmids. A second class of vectors relies upon the integration of the desired gene sequences into the host cell chromosome. The vectors must also incorporate a bacterial origin of replication. Suitable bacterial origins of replication include, for example, the Co/E1, pSC101 and M13 origins of replication.

Expression vectors useful of the present invention typically contain a promoter located 5' to (i.e., upstream of) the DNA sequence to be expressed, and a transcription termination sequence located 3' to (i.e., downstream of) the sequence to be expressed. Suitable promoters include, for example, the yeast ADH1 promoter. The promoter sequence may also be inducible, to allow modulation of expression (e.g., by the presence or absence of nutrients or other inducers in the growth medium). Examples include the yeast GAL1, CUP1, and MET25 promoters. Suitable termination-sequences include, for example, the yeast CYC1 termination and polyadenylation sequences.

The expression vectors may also include other regulatory sequences for optimal expression of the desired product. Such sequences include secretory leader sequences, which provide for secretion of the expressed product or direct membrane localization, and restriction enzyme recognition sequences, which provide sites for cleavage by restriction endonucleases. All of these materials are known in the art and some are commercially available.

A suitable expression vector may also include marking sequences, which allow phenotypic detection and/or selection of transformed yeast or bacterial cells. Such a marker may provide prototrophy to an auxotrophic host (e.g., amino acid biosynthetic genes), biocide resistance or supersensitivity (e.g., antiobiotic resistance) or a phenotypically detectable signal (e.g., fluorescence). The selectable marker gene can be either directly linked to the DNA gene sequences to be expressed, or introduced into the same cell by transformation. Examples of yeast selectable markers include *Basidium pullulans* AUR1-C gene, the *S. cerevisiae* URA3 or LEU2 genes and the like. Examples of bacterial selectable markers include the ampicillin resistance gene. A preferred vector is pYESII, containing the Co/E1 and $2\mu$ origins of replication, the yeast URA3 and bacterial amp$^R$ genes, and the yeast GAL1 promoter sequence (Invitrogen).

In a further alternative, the constructs may be introduced into a cell by transformation in conjunction with a gene allowing for selection where the construct will become integrated into the host genome or persist episomally. Usually, the construct will be part of a vector having homologous sequences for integration or a replication system recognized by the host cell.

Host cells

The present invention additionally concerns hosts for the expression of the N-PAK gene constructs. Suitable host cells are yeasts. Examples include Saccharomyces species (e.g., *S. cerevisiae*), Candida species (e.g., *C. albicans*), and Schizosaccharomyces species (e.g., *S. pombe*) in which endogenous activities do not interfere with the function of the protein under study. Especially preferred is the strain *S. cerevisiae* ATCC 74424 (referred to herein as SGY 1707 or YJG 200-16C). The term "ATCC" as used herein refers to the accession number of the American Type Culture Collection, 12301 Parklawn Drive, Rockville, Md. 20852, the depository for the organism referred to. *Saccharomyces cerevisiae* ATCC 74424 was deposited with the ATCC on Aug. 20, 1997, under the provisions of the Budapest Treaty.

Expression vectors may be introduced into host cells by various methods known in the art. For example, transformation of host cells with expression vectors can be carried out by the alkali cation method. However, other methods for introducing expression vectors into host cells, for example, electroporation and spheroplast transformation can also be employed. Host cells containing an expression vector may be identified by any of a number of methods known in the art.

The protein desired to be expressed in the present invention comprises at least the kinase domain of mammalian N-Pak and does not have the Cdc42 binding domain. Types of N-Pak useful herein include rat, human, murine, and the like. The expression vectors and host cells of the invention may also be engineered to express larger sequences of N-Pak protein which can result in expression of other binding sites such as those that bind to the C-terminal portion (C100) of β-APP. These other binding sites may be desirable for study of the interaction between N-Pak and proteins to which it binds. It is also contemplated that the present invention include functional homologs of the kinase domain of mammalian N-Pak. In this context, "functional homologs" are these peptides that exhibit serine/threonine kinase activity capable of complementing the yeast ste20 deletion. It is preferred that a functional homolog useful herein have at least about 50% homology (i.e., 50% positional similarity or identity) to the kinase domain of rat N-Pak. It has been discovered that expression of the N-Pak kinase domain in yeast in the absence of the Cdc42 binding domain allows for functional substitution for the yeast Ste20 protein in systems in which such substution was heretofore not seen (see Zhao et al, 1995). Therefore, truncation to the N-Pak gene to exclude the Cdc42 binding domain is important to the present invention. The DNA useful herein encoding the kinase domain of N-Pak optionally includes the codons upstream of the kinase domain up to the Cdc42 binding domain. That is, the DNA useful in the present invention optionally encodes the amino acids flanking the N-terminal portion of the kinase domain but does not extend to the Cdc42 binding domain. Thus, in the case of rat N-Pak, the DNA useful herein encodes a peptide that starts anywhere from amino acid number 138 to amino acid number 254 of SEQ ID NO: 2 and stops after the kinase domain, i.e., typically at amino acid number 544 of SEQ ID NO: 2 (all reference to rat N-Pak amino acid position numbers and nucleotide position numbers refer to the rat cDNA and amino acid sequence of N-Pak as disclosed in WO 94/05811). Likewise, in the case of human N-Pak, the DNA useful herein encodes a peptide that starts anywhere from amino acid number 133 to amino acid number 269 of SEQ ID NO: 4 and stops after the the kinase domain, i.e., typically at amino acid number 545 of SEQ ID NO: 4 (all reference to human N-Pak amino acid position numbers and nucleotide position numbers refer to the human cDNA and amino acid sequence of h-Pak1 as disclosed in Brown et al., (1996), *Curr. Biol.*, 6(5):598–605). Thus, a preferred embodiment is when the expression vector of the invention comprises a fragment of the rat N-Pak gene comprising a fragment of the rat N-Pak gene having a sequence starting at nucleotide 412 through nucleotide 760 of SEQ ID NO: 7 and ending at nucleotide 1635 of SEQ ID NO: 1. Similarly, another preferred embodiment is when the expression vector of the invention comprises a fragment of the human N-Pak gene having a sequence starting at nucleotide 451 through nucleotide 859 of SEQ ID NO: 3 and ending at nucleotide 1691 of SEQ ID NO: 3.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 74, 560–564 (1977) may be employed.

It should, of course, be understood that not all expression vectors and DNA regulatory sequences will function equally well to express DNA sequences. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention further concerns an assay method for identifying a compound that interferes with the activity of mammalian N-Pak comprising:

(a) incubating a test compound with a recombinant yeast cell that does not express Ste20 but expresses the kinase domain of N-Pak or functional homolog thereof, and;

(b) determining whether the mating signal transduction pathway of the yeast cell is inhibited relative to a control without the test compound.

In the assay of the invention it is preferred that the recombinant yeast cell does not express the Cdc42 binding domain of N-Pak. The assay of the invention can be performed by introducing a recombinant yeast strain of the invention into a growth medium under conditions resulting in constitutive expression of the N-Pak kinase domain in the presence of a test compound and monitoring the ability of the yeast to mate, using a quantitave mating assay. It is preferred to use a strain that is engineered to express a reporter in addition to the N-Pak kinase domain and then monitor expression of the reporter, thereby obviating the need for a mating phermone or actual mating. In addition, it is also necessary that that the endogenous yeast Ste20 gene be deleted from or otherwise inactivated in the host cell.

The reporters useful herein can be, for example, enzymes such as β-galactosidase, luciferase, green fluorescent protein, and the like.

The assay method of the invention can be used to detect inhibitors of N-Pak kinase activity. Since N-Pak has been shown to bind to the C100 fragment of β-APP in vitro, the assay of the invention can useful to screen for compounds that inhibit the interaction between N-Pak and β-APP C100, provided that the sequence of N-Pak coding for the C100 binding domain is also expressed. The componds so identified are therefore useful in treatment and/or prevention of Alzheimer's Disease. The reporter construct can be altered, such that any desired reporter gene could be employed. This would be placed under the control of a promoter for a gene normally induced by mating, i.e., a gene positively regulated by the transcriptional activator Ste 12. For example, instead of a heterologous gene for a non-essential protein, a yeast gene encoding a biosynthetic enzyme could be used. In a strain deleted for the chromosomal copy of this gene, growth would be dependent upon expression of the reporter gene. A reverse system, whereby expression of the reporter is detremental to the cell, can also be constructed and is contemplated to be within the scope of the present invention. One example would employ the URA3 gene as a reporter. The URA3 gene would be fused to a mating responsive promoter such as FUS1. N-Pak induced signalling through the pathway would allow a ura3, ste20 host strain to grow in the absence of uracil. Inhibition of signalling would result in reduced growth. In the presence of the uracil analogue 5 fluoro-orotic acid (5FOA), Ura$^+$ cells are inhibited, while ura$^-$ cells continue to grow. In this case, signalling through the pathway causes growth inhibition, while inhibition of signalling, by turning off expression of the URA3 reporter, will result in growth on 5-FOA media.

Growth of the host cells may be achieved by one of ordinary skill in the art by the use of an appropriate medium. Appropriate media for growing host cells include those which provide nutrients necessary for the growth of the cells. A typical medium for growth includes necessary carbon sources, nitrogen sources, and trace elements. Inducers may also be added. The term "induce", as used herein, includes any compound enhancing formation of the desired protein or peptide. Carbon sources may include sugars such as glucose, galactose, raffinose, and the like; organic acids such as sodium acetate, and the like; and alcohols such as ethanol. A preferred medium comprises Yeast Nitrogen Base (Difco) containing 2% glucose or 2% galactose and all necessary amino acids. The pH of the medium is preferably adjusted to about 5 to 6, more preferably about 5.

The process of the present invention is performed under conditions suitable for expression of the desired peptide. The pH of the medium is preferably maintained between 4.0 and 6.0, most preferably between 4.5 and 5.5, during the growth of host cells. A suitable temperature range for the process of the invention is from about 28° C. to about 32° C. Pressure is not known to be critical to practice of the invention and for convenience about atmospheric pressure is typically employed. The process of the invention is preferably carried out under aerobic conditions.

The yeast assay of the invention can be used for high throughput screening for agents that inhibit the activity of N-Pak. Inhibition would most probably be due to direct effects on the kinase activity, however, interference with signalling by other mechanisms, such as by altering the conformation of N-Pak such that it has reduced ability to interact with upstream activators or downstream target proteins might also be detected. The present system can also be useful for studying structure-function relationships of the N-Pak protein. It also can be useful for study of the role of the regions 5' of the kinase domain in regulation of activity.

In addition, it could be used to define specific regions that interact with other proteins such as β-APP. The method has utility for identifying compounds that specifically inhibit protein-protein interactions necessary for N-Pak activity. Thus, the compounds indentified by practice of the method of the invention can be useful to treat or prevent degenerative human diseases.

The following examples are further illustrative of the present invention. These examples are not intended to limit the scope of the present invention, and provide further understanding of the invention.

EXAMPLES

MATERIALS AND METHODS:

Strains and strain construction:

The strains of *S. cerevisiae* employed are YSR10 (MATa, can 1-100, ade2-1, his3-11,15, leu2-3,112, tip1-1,ura3-1), YSR30 (MATa ,ste20 1::LEU2, can1-100, ade2-1, his3-11, 15, leu2-3,112, trp1-1,ura3-1) kindly supplied by Dr. S. Ramer (Ramer and Davis, 1993), SY2263 (MATa, ste11::ura3, FUS1/HIS3@his3, FUS1/lacZ@mf2 1, ura3, trp1, leu2, ade1) and SY2068 (MATa, ste7::LEU2, FUS1/HIS3@his3, FUS1/lacZ@mf2 1, ura3, trp1, leu2, ade 1), kindly supplied by Dr. George Sprague. Strain YJG 200-16C, a STE20 derivitive containing the integrated FUS1/lacZ reporter (MATa, ste20 1::LEU2, FUS1/lacZ@mf2 1 ade, his3-11,115, leu2-3,112, trp1, ura3) was derived by crossing strain YSR30 with SY2068. Plasmids were maintained and amplified in *Escherichia coli* strain HB101. All yeast strains were cultivated according to standard methods (Rose et al, 1990 ), using appropriately supplemented Yeast Nitrogen Base (YNB w/o amino acids, Difco) and either glucose or galactose at 2%. Yeast were transformed with plasmid DNA by the alkali cation method, using a commercially prepared kit (Bio 101). Genetic procedures for crossing and tetrad dissection were as described (Rose et al 1990). To obtain a host strain containing, in addition to the STE20 mutation, an integrated FUS1/lacZ reporter, the STE20 strain YSR30 was crossed with SY2068, a STE7 strain containing a FUS1/lacZ reporter integrated into the chromosome. In order to obtain mating between the two sterile strains, the parent strains were each transformed with a plasmid containing a gene which complemented the respective sterile mutation, either pFL (GAL1p/STE20) or pJG204 (GAL1p/STE7). The strains were pregrown on raffinose selective minimal medium, induced with galactose for four hours, then co-plated on rich medium. Diploids were obtained by micromanipulation and propagated on rich medium to allow plasmid loss to occur. Following sporulation, tetrads were dissected for analysis. Fourteen complete tetrads were scored for auxotrophic markers and mating type. As both the STE7 and STE20 gene disruptions were made with LEU2, it was not possible to establish which spore progeny contained the STE7vs STE20 mutation by this analysis. When tested for lacZ by filter assay for β-galactosidase activity, several segregants showed a weak but scorable positive, suggesting that the FUS1/lacZ construct was present in these segregants. PCR analysis of intact yeast cells, done essentially as described by Sathe et al (1991), was used to score the STE20 and STE7 genotypes and confirm the presence of the FUS1/lacZ reporter. To determine the mating type of selected sterile strains, each was first transformed with a plasmid containing the STE20 or STE7 gene, then tested for mating with the Mata and Matα tester strains. A single candiate STE20, STE7, FUS1/lacZ segregant, YJG200-16B, was identified.

Plasmids and plasmid construction:

Plasmid pFLC-1, containing the full length STE20 gene and pSTE20ΔN, containing an N-terminally deleted allele of STE20 (Ramer and Davis, 1993) were kindly supplied by Dr. Sandy Ramer. The STE20ΔN allele encodes a protein which lacks the first 494 amino acids of the protein. The Cdc42 binding domain is absent but the kinase is fully functional and acts in a dominant fashion, giving a mating response in the absence of mating hormone. Each is a 2 μm, URA3 based shuttle vector in which the STE20 gene is regulated by the GAL1 promoter. Plasmid pYES, a 2 μm, URA3 cloning vector (Clonetech) was employed to subclone the N-Pak gene. All plasmid manipulations were done basically by the techniques described in Sambrook et al (1989). Plasmids were transformed into and amplified in *E. coli* strain HB101.

The GAL1 promoter vector, pLL16AΔlac, was constructed by replacing the URA3 gene in the low copy GAL1/lacZ containing plasmid pBM746 with TRP1, deleting the lacZ gene and inserting a polylinker between the BamHI and Sal1 sites originally flanking the lacZ gene. The complete coding sequence of STE7 (Teague et al, 1986) and the kinase domain of STE11 (amino acids 342–717) (Rhodes et al. 1990) were generated as BamHI- Sal1 fragments by PCR and subcloned behind the GAL1 promoter in pLL16A lac. The plasmids are pJG212 (STE11ΔN) and pJG204 (STE7) respectively. As with STE20, an N-terminal deletion of STE11 gives a constitutively activated kinase. The functionality of each of these PCR-generated clones was demonstrated by the ability to restore mating competence to the STE11 or STE7 mutant.

The N-terminally deleted fragment of N-Pak was isolated as a HincII-BamHI fragment (nt 397–1700) and subcloned behind the GAL1 promoter in pYES. (For pJG215-K, pYES was cut with Asp718 made blunt with Klenow and then BamHI cut; in pJG215-L, pYES was cut with HindIII, filled in, then BamHI cut). Each of these constructs is expected to produce a protein initiating at the first ATG downstream of the fusion junction. Thus the translated product will start at the methinione residue which is constitutes amino acid 138 in the full length protein. The promoter/N-PAK junction of each of the plasmids was sequenced to verify the fusion. Note, the protein produced does not contain the Cdc42 binding consensus sequence.

Enzyme assays:

The ability to produce β-galactosidase was initially determined using the filter assay method (Breeden and Nasmyth 1985). Single colonies were streaked onto Whatman 50 filter paper placed on selective minimal agar medium containing either glucose or galactose as carbon source. After a 48–72 hour incubation, the filters were immersed in liquid nitrogen for 30 seconds, air dried and assayed. For this, the filters were placed in petri dishes on top of 3 MM paper which was presoaked in 3.5 ml of reaction mixture per 100 mm dish and incubated at 30° C. for 4 to 24 hours. The reaction mixture contains X-gal (5-bromo-4-chloro-3-indolyl-β-D-galactoside) at 1 mg/ml in Z buffer (Miller, 1972) For quantitative determination, enzyme assays were performed on cell extracts, using the fluorometric substrate methylumbelliferone galactoside.

Quantitative mating assays:

Quantatative mating reactions were performed as described by Sprague (Meth. Enzymol. 194, 1991) with some modification. Strain DC17 (MATa, his) was used as the mating test strain. Cultures were pregrown overnight on selective minimal medium containing 2% raffinose and 0.2% glucose. Galactose to a final concentration of 2% was added and the cultures incubated for an additional four hours to induce gene expression. The cells were resuspended to give $4 \times 10^8$ cells/ml of DC17 and $8 \times 10^7$ cells/ml of the MATa strain to be tested. A 25 µl aliquots of each MATa strain was plated on 5 ml of rich medium contained in a well of a 25 mm diameter well microtiter dish. After the fluid was completely absorbed into the agar, 25 µl of the MATα tester strain was added. This resulted in a 5-fold excess of tester strain. Controls using each strain alone were included. The mating mixtures were incubated for four hours at 30° C., then harvested in 0.5 ml of sterile water, serially diluted and aliquots plated on minimal agar. Only those cells which had formed diploids can grow on minimal medium, as each haploid strain contains different auxotrophic mutations. After incubation at 30° C. for three days, the number of colonies growing on the plates was determined. The frequency of mating is expressed as the total number of diploids formed in the mated sample. Preliminary experiments showed that it was essential to use rich medium and that all fluid placed on the agar must be totally absorbed to obtain mating. As galactose appeared to have a toxic effect on some of the transformed strains, a short galactose induction period was employed.

RESULTS:

The results are in the following tables.

TABLE 1

Quantitative mating analysis of transformed STE20 strains.

| Host strain | Plasmid | (Gene present) | Mating frequency |
|---|---|---|---|
| STE20 | pYES (vector) | | $5.8 \times 10^6$ |
| ste20 | pYES (vector) | | |
| " | pFLC-1 | (STE20) | $1.8 \times 10^5$ |
| " | pSTE20ΔN | (STE20ΔN) | $7.1 \times 10^4$ |
| " | pJG215-K9 | (N-Pak) | $2.3 \times 10^5$ |
| " | pJG215-K21 | (N-Pak) | $2.5 \times 10^5$ |
| " | pJG215-L8 | (N-Pak) | $8.5 \times 10^4$ |
| " | pJG212 | (STE11) | $2.3 \times 10^4$ |
| " | pJG204 | (STE7) | $3.5 \times 10^2$ |

The various transformed haploid strains were tested for mating efficiency as described in Materials and Methods

TABLE 2

Filter assay for β-galactosidase

| Plasmid | Gene | Non-induced | Induced |
|---|---|---|---|
| A. Plasmids in strain YJG200-16C (STE20) | | | |
| pYES | Vector | − | − |
| pJG204 | STE7 | + | − |
| pJG212 | STE11 | + | ++++ |
| pFLC-1 | STE20 | ++ | ++ |
| pSTE20 N | STE20ΔN | − | ++++ |
| pJG215-K-9 | N-PakΔN | + | ++++ |
| pJG215-L-3 | N-PakΔN | + | ++++ |
| pJG215 K-21 | N-PakΔN | + | ++++ |
| B. Plasmids in strain SGY 2263 (ste11) | | | |
| pYES | Vector | − | − |
| pJG204 | STE7 | − | + |
| pJG212 | STE11 | + | ++++ |
| pSTE20 N | STE20N | − | − |
| pJG215-K-9 | N-PakΔN | − | − |
| pJG215-L-3 | N-PakΔN | − | − |
| C. Plasmids in strain YJG200-9A (ste7) | | | |
| pYES | Vector | − | − |
| pJG204 | STE7 | − | ++ |
| pJG212 | STE11 | − | − |
| pSTE20 N | STE20N | − | − |
| pJG215-K-9 | N-PakΔN | − | − |
| pJG215-L-3 | N-PakΔN | − | − |

The number of pluses indicates the relative intensity of the resulting blue color.

TABLE 3

Activation of the mating signal transduction pathway by N-Pak β-galactosidase levels in glucose repressed and galactose induced cultures

| Plasmid | Uninduced | Induced |
|---|---|---|
| pYES | 0.3 | <0.2 |
| pFLC-1 | 17.6 | 7.1 |
| pSTE20-ΔN | 0.2 | 77.2 |
| pJG215-L-3 N-PakΔN | 0.3 | 56.3 |
| pJG215-K-21 N-PakΔN | 0.3 | 57.2 |

All plasmids are in strain YJG200-16C (STE20). Activity is expressed as units per 25 µl aliquot of culture extract ($2.5 \times 10^7$ cells). One unit of enzyme is defined as the amount needed to hydrolyze one picomole of substrate per minute under the standard reaction conditions.

What is claimed is:

1. A recombinant yeast host cell comprising a recombinant nucleic acid encoding the kinase domain of mammalian N-Pak or a functional homolog thereof, wherein when expressed, said kinase domain or functional homolog thereof has serine/threonine kinase activity but not Cdc42 binding activity.

2. The recombinant yeast cell of claim 1 wherein said recombinant nucleic acid is DNA.

3. The recombinant yeast cell of claim 1 wherein said recombinant nucleic acid encodes the kinase domain of mouse, rat, or human N-Pak.

4. The recombinant yeast cell of claim 1, wherein sad recombinant nucleic acid encodes a human N-Pak peptide starting at an amino acid selected from the group consisting of amino acids 133 through 269 and stopping at the end of the kinase domain of human N-Pak, wherein the amino acid sequence of human N-Pak is given in SEQ ID NO: 4.

5. The recombinant yeast cell of claim 1 wherein said recombinant nucleic acid encodes a rat N-Pak peptide starting at an amino acid selected from the group consisting of ammo acids 138 through 254 and stopping at the end of the kinase domain of rat N-Pak, wherein the amino acid sequence of rat N-Pak is given in SEQ ID NO: 2.

6. The recombinant yeast cell of claim 1 wherein said nucleic acid comprises a yeast promoter.

7. The recombinant yeast cell of claim 6 wherein said promoter is the GAL1 promoter.

8. The recombinant yeast cell of claim 1 wherein said nucleic acid further encodes a reporter.

9. The recombinant yeast cell of claim 8 wherein said reporter is a FUS1/lacZ construct.

10. The recombinant yeast cell of claim 1 lacking a functional STE20 gene.

11. The recombinant yeast cell of claim 1 which is a strain of Saccharomyces, Candida, or Schizosaccharomyces.

12. *Saccharomyces cerevisiae* ATCC 74424.

13. An expression vector comprising a yeast promoter and a nucleic acid encoding the kinase domain of a mammalian N-Pak, or functional homolog hereof, wherein when expressed, said kinase domain or functional homolog thereof has serine/threonine kinase activity.

14. The expression vector of claim 13 wherein said nucleic acid is DNA.

15. The expression vector of claim 13 wherein said nucleic acid encodes the kinase domain of mouse, rat, or human N-Pak.

16. The expression vector of claim 13 wherein said nucleic acid encodes a human N-Pak peptide starting at an amino acid selected from the group consisting of amino acids 133 through 269 and stopping at the end of the kinase domain of human N-Pak, wherein the amino acid sequence of human N-Pak is given in SEQ ID NO: 4.

17. The expression vector of claim 13 wherein said nucleic acid encodes a rat N-Pak peptide starting at an amino acid selected from the group consisting of amino acids 138 through 254 and stopping at the end of the kinase domain of rat N-Pak, wherein the amino acid sequence of rat N-Pak is given in SEQ ID NO: 2.

18. The expression vector of claim 13 wherein said promoter is the GAL1 promoter.

19. The expression vector of claim 13 wherein said nucleic acid further encodes a reporter.

20. The expression vector of claim 19 wherein said reporter is a FUS1/lacZ construct.

21. The expression vector of claim 13 wherein said nucleic acid encoding the kinase domain of mammalian N-Pak is a fragment of the rat N-Pak gene consisting of a sequence starting at a nucleotide selected from the group consisting of nucleotide 412 through nucleotide 760, and ending at nucleotide 1635, wherein the nucleic acid sequence of rat N-Pak is given in SEQ ID NO: 1.

22. The expression vector of claim 13 wherein said nucleic acid encoding the kinase domain of mammalian N-Pak is a fragment of the human N-Pak gene consisting of a sequence starting at a nucleotide selected from the group consisting of nucleotide 451 through nucleotide 859, and ending at nucleotide 1691, wherein the nucleic acid sequence of human N-Pak is given in SEQ ID NO: 3.

23. The expression vector of claim 13 which is a plasmid.

24. Plasmids pJG215-K9, pJG215-K21, and pJG215-L8.

* * * * *

SEQUENCE LISTING

<160> NUMBER OF SEQ ID NOS: 4

<210> SEQ ID NO 1
<211> LENGTH: 1635
<212> TYPE: DNA
<213> ORGANISM: Rattus exulans

<400> SEQUENCE: 1
atgtctgaca gcttggataa cgaagaaaaa cctccagctc ccccactgag gatgaacagt    60
aacaaccgag attcttcagc actcaaccac agctccaaac cactgcccat ggccccggaa   120

-continued

```
gagaagaata agaaagccag gcttcgctct atcttcccag gaggagggga taaaaccaat      180
aagaagaaag agaaagaacg cccagagatc tctcttcctt cagactttga gcatacgatt      240
catgtgggtt ttgatgcagt caccgggaa ttcactggaa ttcctgaaca atgggctcga       300
ctgctccaaa cctccaacat acaaaactg gaacagaaga agaacccaca ggctgttctg       360
gatgttctca gtttacga ctccaaagaa acagtcaaca accagaaata catgagcttt        420
acatcaggag ataaaagtgc ccatggatat atagcagcac atcagtcgaa taccaaaaca     480
gcttcagaac ctcctttggc tcctcctgta tctgaagaag aggatgaaga agaggaagag     540
gaagaagatg ataatgagcc cccgcctgtc attgcaccaa gaccagagca tacaaaatca    600
atctatactc gttctgtggt tgagtcaatt gcttcaccag cagcaccaaa taagaagcc     660 acccacctt ctgctgagaa tgccaattcc agtactttgt acaggaatac agatcggcaa     720
agaaaaaaat ccaagatgac agatgaggag atcctagaga agctaagaag cattgtgagt   780
gttggggacc caaagaagaa atatacaaga tttgaaaaaa ttggccaagg ggcatcagga    840 actgttttaca cagcactaga cattgcgaca ggacaagagg tggctataaa gcaaatgaac   900
cttcaacagc agcccaaaaa ggaattaatt attaatgaaa ttcttgtcat gagggaaaat    960
aagaacccca atattgtcaa ttatttagat agctacttag tgggtgatga actgtgggta   1020
gtcatggaat acttggctgg tggctctttg actgacgtgg tcacagaaac ctgtatggat   1080
gaaggacaga tagcagccgt ctgtagagag tgcctccaag ctttggattt cttgcactca   1140
aaccaagtga tccacagaga tataaagatg gacaatattc tcctcgggat ggatggttct   1200
gttaaactga ctgattttgg attctgtgcc caaatcactc ctgagcaaag taaacgaagc   1260
actatggtgg gaactcccta ttggatggca cctgaggtgg taactcgaaa agcttatggc   1320
ccgaaagttg atatctggtc tctgggaatc atggccattg aaatggtgga aggtgaaccc   1380 ccttaccta atgaaaatcc actcaggggc ttatatctga tagccactaa tggaaccccca  1440 gagctccaga atcccgagag actgtcagct gtattccgtg acttcttaaa tcgctgtctt   1500
gagatggatg tggatagacg agggtctgcc aaggagcttt tgcagcatcc atttttaaaa   1560
ttagccaagc ccctgtccag cctcactcct ctgattcttg ctgcaaagga agccattaag   1620
aacagtagcc gttag                                                     1635
```

<210> SEQ ID NO 2
<211> LENGTH: 544
<212> TYPE: PRT
<213> ORGANISM: Rattus exulans

<400> SEQUENCE: 2

```
Met Ser Asp Ser Leu Asp Asn Glu Glu Lys Pro Pro Ala Pro Pro Leu
 1               5                  10                  15

Arg Met Asn Ser Asn Asn Arg Asp Ser Ser Ala Leu Asn His Ser Ser
            20                  25                  30

Lys Pro Leu Pro Met Ala Pro Glu Glu Lys Asn Lys Lys Ala Arg Leu
        35                  40                  45

Arg Ser Ile Phe Pro Gly Gly Gly Asp Lys Thr Asn Lys Lys Lys Glu
    50                  55                  60

Lys Glu Arg Pro Glu Ile Ser Leu Pro Ser Asp Phe Glu His Thr Ile
65                  70                  75                  80

His Val Gly Phe Asp Ala Val Thr Gly Glu Phe Thr Gly Ile Pro Glu
                85                  90                  95

Gln Trp Ala Arg Leu Leu Gln Thr Ser Asn Ile Thr Lys Leu Glu Gln
            100                 105                 110
```

-continued

```
Lys Lys Asn Pro Gln Ala Val Leu Asp Val Leu Lys Phe Tyr Asp Ser
        115                 120                 125
Lys Glu Thr Val Asn Asn Gln Lys Tyr Met Ser Phe Thr Ser Gly Asp
    130                 135                 140
Lys Ser Ala His Gly Tyr Ile Ala Ala His Gln Ser Asn Thr Lys Thr
145                 150                 155                 160
Ala Ser Glu Pro Pro Leu Ala Pro Pro Val Ser Glu Glu Asp Glu
                165                 170                 175
Glu Glu Glu Glu Glu Glu Asp Asp Asn Glu Pro Pro Val Ile Ala
            180                 185                 190
Pro Arg Pro Glu His Thr Lys Ser Ile Tyr Thr Arg Ser Val Val Glu
        195                 200                 205
Ser Ile Ala Ser Pro Ala Ala Pro Asn Lys Glu Ala Thr Pro Pro Ser
    210                 215                 220
Ala Glu Asn Ala Asn Ser Ser Thr Leu Tyr Arg Asn Thr Asp Arg Gln
225                 230                 235                 240
Arg Lys Lys Ser Lys Met Thr Asp Glu Glu Ile Leu Glu Lys Leu Arg
                245                 250                 255
Ser Ile Val Ser Val Gly Asp Pro Lys Lys Tyr Thr Arg Phe Glu
            260                 265                 270
Lys Ile Gly Gln Gly Ala Ser Gly Thr Val Tyr Thr Ala Leu Asp Ile
        275                 280                 285
Ala Thr Gly Gln Glu Val Ala Ile Lys Gln Met Asn Leu Gln Gln Gln
    290                 295                 300
Pro Lys Lys Glu Leu Ile Ile Asn Glu Ile Leu Val Met Arg Glu Asn
305                 310                 315                 320
Lys Asn Pro Asn Ile Val Asn Tyr Leu Asp Ser Tyr Leu Val Gly Asp
                325                 330                 335
Glu Leu Trp Val Val Met Glu Tyr Leu Ala Gly Gly Ser Leu Thr Asp
            340                 345                 350
Val Val Thr Glu Thr Cys Met Asp Glu Gly Gln Ile Ala Ala Val Cys
        355                 360                 365
Arg Glu Cys Leu Gln Ala Leu Asp Phe Leu His Ser Asn Gln Val Ile
    370                 375                 380
His Arg Asp Ile Lys Met Asp Asn Ile Leu Leu Gly Met Asp Gly Ser
385                 390                 395                 400
Val Lys Leu Thr Asp Phe Gly Phe Cys Ala Gln Ile Thr Pro Glu Gln
                405                 410                 415
Ser Lys Arg Ser Thr Met Val Gly Thr Pro Tyr Trp Met Ala Pro Glu
            420                 425                 430
Val Val Thr Arg Lys Ala Tyr Gly Pro Lys Val Asp Ile Trp Ser Leu
        435                 440                 445
Gly Ile Met Ala Ile Glu Met Val Glu Gly Glu Pro Pro Tyr Leu Asn
    450                 455                 460
Glu Asn Pro Leu Arg Ala Leu Tyr Leu Ile Ala Thr Asn Gly Thr Pro
465                 470                 475                 480
Glu Leu Gln Asn Pro Glu Arg Leu Ser Ala Val Phe Arg Asp Phe Leu
                485                 490                 495
Asn Arg Cys Leu Glu Met Asp Val Asp Arg Arg Gly Ser Ala Lys Glu
            500                 505                 510
Leu Leu Gln His Pro Phe Leu Lys Leu Ala Lys Pro Leu Ser Ser Leu
        515                 520                 525
```

-continued

Thr Pro Leu Ile Leu Ala Ala Lys Glu Ala Ile Lys Asn Ser Ser Arg
    530                 535                 540

<210> SEQ ID NO 3
<211> LENGTH: 1740
<212> TYPE: DNA
<213> ORGANISM: Homo sapiens

<400> SEQUENCE: 3

| | | | | | |
|---|---|---|---|---|---|
| ggagagccga | gaggagctga | gcgagcgcgg | aagtagctgc | tgctggtggt | gacaatgtca | 60 |
| aataacggcc | tagacattca | agacaaaccc | ccagccccctc | cgatgagaaa | taccagcact | 120 |
| atgattggag | ccggcagcaa | agatgctgga | accctaaacc | atggttctaa | acctctgcct | 180 |
| ccaaacccag | aggagaagaa | aaagaaggac | cgatttttacc | gatccatttt | acctggagat | 240 |
| aaaacaaata | aaagaaaga  | gaaagagcgg | ccagagattt | ctctccctttc | agattttgaa | 300 |
| cacacaattc | atgtcggttt | tgatgctgtc | acagggagt | ttaccggaat | gccagagcag | 360 |
| tgggcccgct | tgcttcagac | atcaaatatc | actaagtcgg | agcagaagaa | aaacccgcag | 420 |
| gctgttctgg | atgtgttgga | gttttacaac | tcgaagaaga | catccaacag | ccagaaatac | 480 |
| atgagctttta | cagataagtc | agctgaggat | tacaattctt | ctaatgcctt | gaatgtgaag | 540 |
| gctgtgtctg | agactcctgc | agtgccacca | gtttcagaag | atgaggatga | tgatgatgat | 600 |
| gatgctaccc | caccaccagt | gattgctcca | cgcccagagc | acacaaaatc | tgtatacaca | 660 |
| cggtctgtga | ttgaaccact | tcctgtcact | ccaactcggg | acgtggctac | atctcccatt | 720 |
| tcacctactg | aaaataacac | cactccacca | gatgctttga | cccttaatac | tgagaagcag | 780 |
| aagaagaagc | ctaaaatgtc | tgatgaggag | atcttggaga | aattacgaag | catagtgagt | 840 |
| gtgggcgatc | ctaagaagaa | atatacacgg | tttgagaaga | ttggacaagg | tgcttcaggc | 900 |
| accgtgtaca | cagcaatgga | tgtggccaca | ggacaggagg | tggccattaa | gcagatgaat | 960 |
| cttcagcagc | agcccaagaa | agagctgatt | attaatgaga | tcctggtcat | gagggaaaac | 1020 |
| aagaacccaa | acattgtgaa | ttacttggac | agttacctcg | tgggagatga | gctgtgggtt | 1080 |
| gttatggaat | acttggctgg | aggctccttg | acagatgtgt | tgacagaaac | ttgcatggat | 1140 |
| gaaggccaaa | ttgcagctgt | gtgccgtgag | tgtctgcagg | ctctggagtc | tttgcattcg | 1200 |
| aaccaggtca | ttcacagaga | catcaagagt | gacaatattc | tgttgggaat | ggatggctct | 1260 |
| gtcaagctaa | ctgactttgg | attctgtgca | cagataaccc | cagagcagag | caaacggagc | 1320 |
| accatggtag | aaccccata  | ctggatggca | ccagaggttg | tgacacgaaa | ggcctatggg | 1380 |
| cccaaggttg | acatctggtc | cctgggcatc | atggccatcg | aaatgattga | agggagcct  | 1440 |
| ccatacctca | atgaaaaccc | tctgagagcc | ttgtacctca | ttgccaccaa | tgggacccca | 1500 |
| gaacttcaga | acccagagaa | gctgtcagct | atcttccggg | actttctgaa | ccgctgtctc | 1560 |
| gagatggatg | tggagaagag | aggttcagct | aaagagctgc | tacagcatca | attcctgaag | 1620 |
| attgccaagc | ccctctccag | cctcactcca | ctgattgctg | cagctaagga | ggcaacaaag | 1680 |
| aacaatcact | aaaaccacac | tcaccccagc | ctcattgtgc | caagccttct | gtgagataaa | 1740 |

<210> SEQ ID NO 4
<211> LENGTH: 545
<212> TYPE: PRT
<213> ORGANISM: Homo sapiens

<400> SEQUENCE: 4

Met Ser Asn Asn Gly Leu Asp Ile Gln Asp Lys Pro Pro Ala Pro Pro
  1               5                  10                  15

-continued

| | | | | | | | | | | | |
|---|---|---|---|---|---|---|---|---|---|---|---|
|Met|Arg|Asn|Thr|Ser|Thr|Met|Ile|Gly|Ala|Gly|Ser|Lys|Asp|Ala|Gly|
| | |20| | | |25| | | |30| |

Positions 20, 25, 30, 35, 40, 45, ... shown as sequence numbering.

```
Met Arg Asn Thr Ser Thr Met Ile Gly Ala Gly Ser Lys Asp Ala Gly
             20              25              30

Thr Leu Asn His Gly Ser Lys Pro Leu Pro Asn Pro Glu Glu Lys
         35              40              45

Lys Lys Lys Asp Arg Phe Tyr Arg Ser Ile Leu Pro Gly Asp Lys Thr
 50              55              60

Asn Lys Lys Lys Glu Lys Glu Arg Pro Glu Ile Ser Leu Pro Ser Asp
 65              70              75              80

Phe Glu His Thr Ile His Val Gly Phe Asp Ala Val Thr Gly Glu Phe
             85              90              95

Thr Gly Met Pro Glu Gln Trp Ala Arg Leu Leu Gln Thr Ser Asn Ile
             100             105             110

Thr Lys Ser Glu Gln Lys Asn Pro Gln Ala Val Leu Asp Val Leu
         115             120             125

Glu Phe Tyr Asn Ser Lys Thr Ser Asn Ser Gln Lys Tyr Met Ser
         130             135             140

Phe Thr Asp Lys Ser Ala Glu Asp Tyr Asn Ser Ser Asn Ala Leu Asn
 145             150             155             160

Val Lys Ala Val Ser Glu Thr Pro Ala Val Pro Pro Val Ser Glu Asp
             165             170             175

Glu Asp Asp Asp Asp Asp Ala Thr Pro Pro Val Ile Ala Pro
             180             185             190

Arg Pro Glu His Thr Lys Ser Val Tyr Thr Arg Ser Val Ile Glu Pro
             195             200             205

Leu Pro Val Thr Pro Thr Arg Asp Val Ala Thr Ser Pro Ile Ser Pro
             210             215             220

Thr Glu Asn Asn Thr Thr Pro Pro Asp Ala Leu Thr Leu Asn Thr Glu
 225             230             235             240

Lys Gln Lys Lys Pro Lys Met Ser Asp Glu Ile Leu Glu Lys
             245             250             255

Leu Arg Ser Ile Val Ser Val Gly Asp Pro Lys Lys Tyr Thr Arg
             260             265             270

Phe Glu Lys Ile Gly Gln Gly Ala Ser Gly Thr Val Tyr Thr Ala Met
             275             280             285

Asp Val Ala Thr Gly Gln Glu Val Ala Ile Lys Gln Met Asn Leu Gln
 290             295             300

Gln Gln Pro Lys Lys Glu Leu Ile Ile Asn Glu Ile Leu Val Met Arg
 305             310             315             320

Glu Asn Lys Asn Pro Asn Ile Val Asn Tyr Leu Asp Ser Tyr Leu Val
             325             330             335

Gly Asp Glu Leu Trp Val Val Met Glu Tyr Leu Ala Gly Gly Ser Leu
             340             345             350

Thr Asp Val Val Thr Glu Thr Cys Met Asp Gly Gln Ile Ala Ala
             355             360             365

Val Cys Arg Glu Cys Leu Gln Ala Leu Glu Ser Leu His Ser Asn Gln
 370             375             380

Val Ile His Arg Asp Ile Lys Ser Asp Asn Ile Leu Leu Gly Met Asp
 385             390             395             400

Gly Ser Val Lys Leu Thr Asp Phe Gly Phe Cys Ala Gln Ile Thr Pro
             405             410             415

Glu Gln Ser Lys Arg Ser Thr Met Val Gly Thr Pro Tyr Trp Met Ala
             420             425             430

Pro Glu Val Val Thr Arg Lys Ala Tyr Gly Pro Lys Val Asp Ile Trp
             435             440             445
```

```
Ser Leu Gly Ile Met Ala Ile Glu Met Ile Glu Gly Glu Pro Pro Tyr
    450             455             460

Leu Asn Glu Asn Pro Leu Arg Ala Leu Tyr Leu Ile Ala Thr Asn Gly
465             470             475             480

Thr Pro Glu Leu Gln Asn Pro Glu Lys Leu Ser Ala Ile Phe Arg Asp
            485             490             495

Phe Leu Asn Arg Cys Leu Glu Met Asp Val Glu Lys Arg Gly Ser Ala
            500             505             510

Lys Glu Leu Leu Gln His Gln Phe Leu Lys Ile Ala Lys Pro Leu Ser
        515             520             525

Ser Leu Thr Pro Leu Ile Ala Ala Lys Glu Ala Thr Lys Asn Asn
        530             535             540

His
545
```